(12) United States Patent
Dalla Pria et al.

(10) Patent No.: US 9,867,710 B2
(45) Date of Patent: Jan. 16, 2018

(54) MODULAR HUMERAL PROSTHESIS

(71) Applicant: LIMACORPORATE S.P.A., San Daniele del Friuli (IT)

(72) Inventors: Paolo Dalla Pria, Udine (IT); Michele Pressacco, Udine (IT); Simone Ursella, Majano (IT)

(73) Assignee: LIMACORPORATE S.P.A., San Daniele del Friuli (IT)

( * ) Notice: Subject to any disclaimer, the term of this patent is extended or adjusted under 35 U.S.C. 154(b) by 12 days.

(21) Appl. No.: 14/896,309

(22) PCT Filed: Jun. 6, 2014

(86) PCT No.: PCT/IB2014/062002
§ 371 (c)(1),
(2) Date: Dec. 4, 2015

(87) PCT Pub. No.: WO2014/195909
PCT Pub. Date: Dec. 11, 2014

(65) Prior Publication Data
US 2016/0128841 A1  May 12, 2016

(30) Foreign Application Priority Data
Jun. 6, 2013 (IT) .............................. UD2013A0080

(51) Int. Cl.
*A61F 2/40* (2006.01)
*A61F 2/30* (2006.01)

(52) U.S. Cl.
CPC .......... *A61F 2/4014* (2013.01); *A61F 2/4059* (2013.01); *A61F 2002/30337* (2013.01);
(Continued)

(58) Field of Classification Search
CPC .................. A61F 2/4014; A61F 2/4059; A61F 2002/3652; A61F 2002/3674;
(Continued)

(56) References Cited

U.S. PATENT DOCUMENTS 6,524,342 B1 * 2/2003 Muhlhausler ......... A61F 2/4059
623/19.14
2005/0125067 A1   6/2005 Sweeney

FOREIGN PATENT DOCUMENTS

EP   1 472 999 A1   11/2004
WO   WO-99/47081 A1   9/1999

OTHER PUBLICATIONS

Search Report and Written Opinion for PCT/IB2014/062002, dated Sep. 4, 2014.

* cited by examiner

*Primary Examiner* — Thomas J Sweet
*Assistant Examiner* — Megan Wolf
(74) *Attorney, Agent, or Firm* — Marshall, Gerstein & Borun LLP (57) ABSTRACT

A modular humeral prosthesis suitable for implant in a humeral seating of a humerus comprises an articulation component, a distal joint element able to be inserted into said humeral seating along an insertion axis, and an adapter body provided with a support positionable in the humeral seating and that has a coupling seating to connect said articulation component and provided with a connection unit inserted into said support to connect said distal joint element to said adapter body in a releasable manner. The connection unit comprises a clamping element associated in a selectively releasable manner to the distal joint element and the support has a through coupling seating configured to receive and position said clamping element inside it, and also configured to allow the insertion and extraction of said distal (Continued)

joint element through said support without removing said support from the humeral seating.

16 Claims, 4 Drawing Sheets

(52) U.S. Cl.
CPC ............... *A61F 2002/30405* (2013.01); *A61F 2002/30507* (2013.01); *A61F 2002/30604* (2013.01); *A61F 2002/30607* (2013.01); *A61F 2002/404* (2013.01); *A61F 2002/4022* (2013.01); *A61F 2002/4029* (2013.01); *A61F 2002/4044* (2013.01); *A61F 2002/4051* (2013.01)

(58) Field of Classification Search
CPC ...... A61F 2002/4022; A61F 2002/4029; A61F 2002/4033; A61F 2002/4044; A61F 2002/4048; A61F 2002/4074
See application file for complete search history.

fig. 3

MODULAR HUMERAL PROSTHESIS

FIELD OF THE INVENTION

The present invention concerns a humeral prosthesis, able to be configured anatomically or inversely for the reconstruction of the humerus in the articulation of the shoulder. In particular the humeral prosthesis of the present invention is the modular type and comprises an articulation component, a distal joint element and an adapter body which acts as a metaphyseal module.

BACKGROUND OF THE INVENTION

It is known that arthroprostheses used to reconstruct the shoulder joint can be the anatomical or inverse type. Anatomical humeral prostheses are provided with a hemispherical head that artificially reconstructs the human anatomy and are suitable to articulate in the glenoid cavity of the shoulder blade or possibly in a mating artificial seating attached to the glenoid cavity. On the contrary, inverse prostheses provide a concave articular insert able to allow the rotation of an artificial spherical body attached to the glenoid seating, commonly called glenosphere.

It is known that humeral prostheses, whether anatomical or inverse, generally include a distal joint element, also called rod or pin, inserted inside the humerus along the diaphyseal axis, to support the humeral head in anatomical humeral prostheses or the concave articular insert in inverse prostheses.

Distal joint elements of various types are known, for example with an elongated tubular shape, to define an elongated rod, or a small-sized pin, typically used for mini-invasive humeral prostheses. The shape and size of the distal joint element can also depend on the type and size of the humeral prosthesis, for example inverse humeral prostheses can need a distal joint element that is bigger than anatomical ones.

It is possible, for example due to degeneration of the tissues of the shoulder, that operations may have to be carried out to revise the prosthesis, for example to replace the prosthesis, or operations to convert an anatomical prosthesis into a inverse prosthesis or vice versa.

It is known, for example from the patent application EP-A-1.472.999, to make a modular humeral prosthesis, comprising an adapter body, which functions as a metaphyseal module, to be positioned in a seating made under the head of the humerus and connectable on one side to a rod inserted in the humerus and on the other side to the semispherical humeral head, in the case of anatomical prostheses, or to the concave articular insert in the case of inverse prostheses. Indeed, by varying the adapter body, the known modular humeral prosthesis can be made as anatomical or inverse. Moreover, in the field of the same type of prosthesis, anatomical or inverse, it may be possible to change the shape or size of the adapter body, releasing it from the rod and keeping the latter inserted in the humerus, whenever its sizes or characteristics are suitable for the humeral prosthesis to be grafted.

However, one possible disadvantage of this known modular humeral prosthesis is that it cannot be converted from anatomical to inverse without having to replace the adapter body. This latter operation, which entails extracting the adapter body from the bone seating, can be invasive and destructive.

Another possible disadvantage of the known humeral prosthesis is that it does not allow to completely replace the rod with another element inserted in the humerus, such as a rod with a different conformation or size, or a nail for osteosynthesis, preserving the adapter body already inserted, that is, without extracting the adapter body from the humerus which, as we said above, can be difficult and invasive.

It is known for example that, in the event of fractures of the humerus, for the purposes of osteosynthesis, it may be necessary to introduce inside the humerus a humeral nail that reproduces the correct alignment of the bone fragments to allow reciprocal welding thereof. The humeral nail can be introduced in antegrade fashion, with a passage through the proximal part of the humerus (antegrade nail), or retrograde, through an aperture in the olecranon fossa (retrograde nail). The antegrade solution is generally preferable, since it is less invasive and less complex.

However, in the state of the art and with the humeral prostheses available, if there is a fracture of the humerus and there is a humeral prosthesis present, it may be necessary to completely remove the prosthetic implant, or alternatively to use external synthesis means, such as osteosynthesis plates which in any case do not always guarantee a successful synthesis.

One disadvantage of known solutions is therefore that it is not possible to act in an antegrade manner to remove the rod or pin and insert the nail without removing the adapter body, in the event of fractures of the humerus where there is a humeral prosthesis present.

Document US-A-2005/0125067 describes a modular prosthesis of the known type, provided with a head and a rod coupled to the head. The rod has a proximal portion coupled with the head and a distal portion configured to extend in a long bone of the patient. The distal portion can be removed from the rod after the prosthesis has been implanted, without removing the proximal portion.

Document WO-A-99/47081 also describes a modular orthopedic prosthesis having a body that has a through hole that receives a connection bushing that in turn receives a rod having a proximal neck and a distal shaft. The connection bushing can be expanded radially in order to clamp the rod and the body together.

Purpose of the present invention is to obtain a modular humeral prosthesis that allows revisions or conversions of the prosthesis, keeping the adapter body of the humeral prosthesis in the humeral seating and allowing to replace the distal joint element, either rod or pin.

SUMMARY OF THE INVENTION

The present invention is set forth and characterized in the independent claim, while the dependent claims describe other characteristics of the invention or variants to the main inventive idea.

In accordance with the above purpose, a modular humeral prosthesis according to the present invention, which overcomes the limits of the state of the art and eliminates the defects therein, is suitable to be implanted in a humeral seating of a humerus and comprises an articulation component and a distal joint element insertable in the humeral seating along an insertion axis. The humeral prosthesis also comprises an adapter body, which acts as a metaphyseal module, provided with a support that can be positioned in the humeral seating and that has a coupling seating to connect the articulation component and provided with a connection unit inserted into the adapter body support to connect the distal joint element to the adapter body in a releasable manner.

According to the present invention, the connection unit comprises a clamping element associated in a selectively releasable manner to the distal joint element.

Moreover, the adapter body support has a through coupling seating configured to receive and position the clamping element inside it. The through coupling seating is also configured to allow the insertion and extraction of the distal joint element through the adapter body support, without removing the support from the humeral seating.

In this way, allowing the complete passage, or crossing, of the distal joint element along the through coupling seating, it is possible, once the clamping element is removed, to position and remove the distal joint element as well, operating advantageously from above, without needing to extract the adapter body support from the humeral seating.

Therefore, with the present invention, it is possible to carry out revision or conversion operations of the prosthesis maintaining the adapter body support of the humeral prosthesis in the humeral seating. In particular, with the present invention, it is possible to change the articulation component, for the conversion for example from anatomical prosthesis to inverse prosthesis or vice versa, without extracting the adapter body support. Moreover, with the present invention it is also possible to replace the distal joint element, rod or pin, also maintaining in this case the adapter body support of the humeral prosthesis in the seating on the head of the humerus. For example, in the case of conversion of the prosthesis, it might be necessary to change the type or size of the distal joint element, while in the case of a fracture of the humerus for example, in the presence of a modular prosthesis which has already been implanted, it could be necessary to insert an osteosynthesis nail in its place, and in any case the present invention allows to intervene to remove and/or replace the distal joint element operating from above in an antegrade manner, without removing the adapter body support.

In variant forms of embodiment, the clamping element is configured to clamp a movement of axial extraction of the distal joint element toward the outside of the humeral seating.

In variant forms of embodiment, the clamping element is configured to achieve a same-shape coupling with a one-directional constraint toward the inside of the humeral seating with the through coupling seating of the support.

In variant forms of embodiment, the clamping element is configured to achieve a same-shape coupling with a one-directional constraint toward the outside of the humeral seating with the distal joint element.

In variant forms of embodiment, the clamping element is coupled externally to the distal joint element.

In variant forms of embodiment, the clamping element has a truncated cone configuration, both internally and externally. The truncated cone configuration can be inverted between outside and inside. For example, the clamping element can be shaped internally like a truncated cone, while externally it can be shaped like a truncated cone inverse with respect to the inside.

In possible implementations, the clamping element comprises a hollow truncated cone element that has an external clamping surface shaped like a truncated cone with a section that reduces toward the inside of the humeral seating, an internal clamping cavity delimited by internal lateral walls shaped like a truncated cone inverse with respect to the external clamping surface, to receive a mating connection portion of the distal joint element.

In other variant forms of embodiment, internally the clamping element has a truncated cone configuration and externally a cylindrical configuration.

In yet other variant forms of embodiment, internally the clamping element has a cylindrical configuration and externally a truncated cone configuration.

In implementations where the clamping element is at least internally configured as a truncated cone, the distal joint element has a similar truncated cone connection portion to be inserted into the clamping element.

In other variant forms of embodiment, the clamping element has a cylindrical configuration, both internally and externally.

In a possible implementation, internally the clamping element has threaded connection means to cooperate with the distal joint element. This implementation can be used, for example, in the case where the clamping element internally has a cylindrical configuration and the distal joint element has a similar cylindrical connection portion to be inserted in the clamping element.

Depending whether the clamping element is externally configured as a truncated cone or as a cylinder, the through coupling seating will consequently be configured as a truncated cone or a cylinder.

Moreover, according to some forms of embodiment of the present invention, the connection unit comprises an anchoring element configured to clamp a movement of axial extraction of the clamping element toward the outside of the humeral seating.

The anchoring element can be configured to be constrained bi-directionally to the adapter body support.

In possible variation forms of embodiment, the anchoring element comprises an externally threaded annular body that has an external threaded anchoring surface and a shaped central aperture.

In other variants, the anchoring element comprises an elastically deformable ring, in particular a Seeger ring.

In some forms of embodiment, the clamping element is inserted between the distal joint element and the anchoring element.

In some forms of embodiment of the present invention, the connection unit also comprises an attachment element associated with the clamping element and the distal joint element to clamp the axial movement thereof toward the inside of the humeral seating with respect to the clamping element.

In possible variants, the attachment element is mounted on the clamping element and is attached to the distal joint element.

In some forms of embodiment, the attachment element comprises a screw, provided with a shaped head, configured to abut against the clamping element, from which a threaded rod extends, configured to be inserted into the clamping element and able to be screwed into an attachment cavity of the distal joint element to define overall a one-directional constraint of the distal joint element toward the inside of the humeral seating.

Moreover, in possible variants, the clamping element is configured to define an axial stopping abutment for the attachment element.

These and other aspects, characteristics and advantages of the present disclosure will be better understood with reference to the following description, drawings and attached claims. The drawings, which are integrated and form part of the present description, show some forms of embodiment of the present invention, and together with the description, are intended to describe the principles of the disclosure.

The various aspects and characteristics described in the present description can be applied individually where possible. These individual aspects, for example aspects and characteristics described in the attached dependent claims, can be the object of divisional applications.

It is understood that any aspect or characteristic that is discovered, during the patenting process, to be already known, shall not be claimed and shall be the object of a disclaimer.

BRIEF DESCRIPTION OF THE DRAWINGS

These and other characteristics of the present invention will become apparent from the following description of some forms of embodiment, given as a non-restrictive example with reference to the attached drawings wherein.

To facilitate comprehension, the same reference numbers have been used, where possible, to identify identical common elements in the drawings. It is understood that elements and characteristics of one form of embodiment can conveniently be incorporated into other forms of embodiment without further clarifications.

DETAILED DESCRIPTION OF FORMS OF EMBODIMENT

We shall now refer in detail to the various forms of embodiment of the present invention, of which one or more examples are shown in the attached drawing. Each example is supplied by way of illustration of the invention and shall not be understood as a limitation thereof. For example, the characteristics shown or described insomuch as they are part of one form of embodiment can be adopted on, or in association with, other forms of embodiment to produce another form of embodiment. It is understood that the present invention shall include all such modifications and variants.

Figure 1:
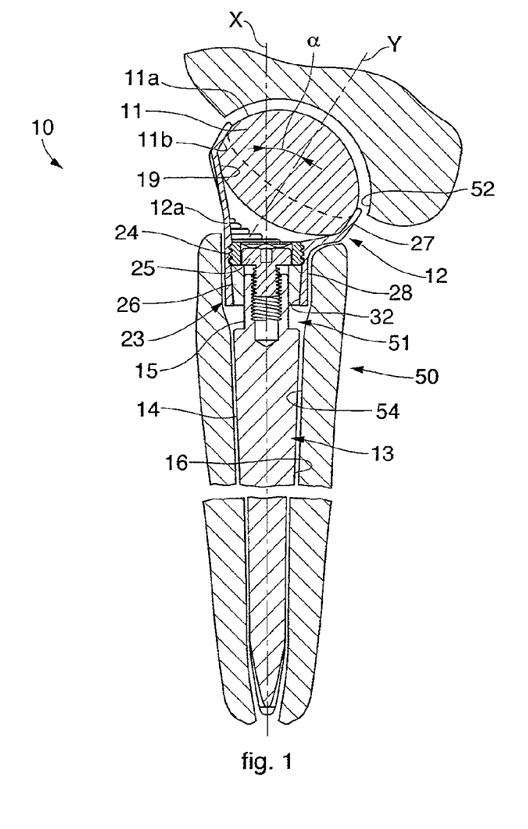
FIG. 1 is a section of a modular humeral prosthesis, in its anatomical configuration, according to forms of embodiment of the present invention.
Figure 2:
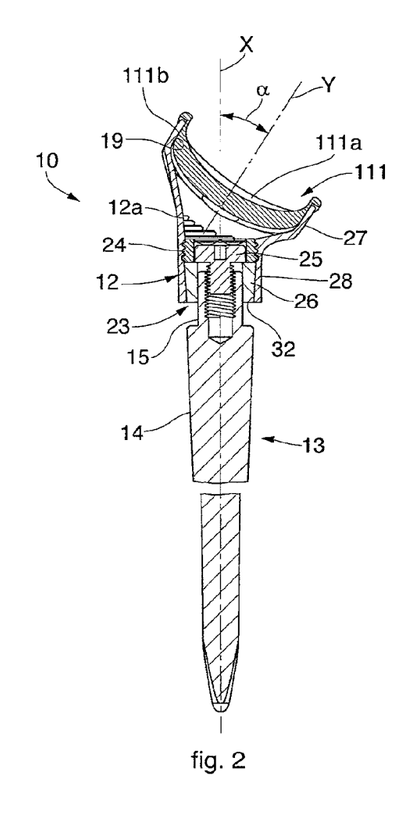
FIG. 2 is a section of a modular humeral prosthesis, in its inverse configuration, according to forms of embodiment of the present invention.

FIGS. 1 and 2 are used to describe forms of embodiment of a modular humeral prosthesis 10 suitable to be implanted in a humeral seating 51 of a humerus 50.

The modular humeral prosthesis 10 can comprise, or be associated with, an articulation component that can be a humeral head 11 for example, or a concave articular insert 111, depending on whether the modular humeral prosthesis 10 is anatomical or inverse, a distal joint element 13, 113 and an adapter body 12.

According to some forms of embodiment of the present invention, the distal joint element 13, 113 can have an axial symmetry with respect to an insertion axis X. The axis X can generally coincide with the diaphyseal axis along which the distal joint element 13, 113 is located in the humerus 50, even if situations can be hypothesized wherein the insertion axis X does not coincide with the diaphyseal axis.

In some forms of embodiment, the modular humeral prosthesis 10 is generally inserted in the direction defined by the axis X, toward the inside of the humerus 50, and also extracted in the direction defined by the axis X, however in the opposite direction, that is toward the outside of the humerus 50 and the humeral seating 51.

In some forms of embodiment, the adapter body 12 is intended to be positioned in the humeral seating 51, typically along the axis X, and can be connected on one side to the distal joint element 13, 113, insertable in its turn in the humerus 50, and on the other side, opposite to the articulation component, to the humeral head 11, or concave articular insert 111. The adapter body 12 can also be configured to allow the bone integration with the internal surface of the humeral seating 51.

In some forms of embodiment, the adapter body 12 is the modular type, comprising components, including for example the following, indicated by the reference numbers 12a and 23, that can be coupled to each other in a selectively releasable manner, according to requirements.

In particular, in possible implementations the adapter body 12 can comprise a support 12a to support the articulation component, humeral head 11, or concave articular insert 111. The support 12a of the adapter body 12 can typically be inserted in a stable manner into the humeral seating 51.

In some forms of embodiment, the adapter body 12 can also comprise a connection unit 23 for the releasable connection of the distal joint element 13, 113 to the support 12a. In possible implementations, the connection unit 23 can be axial-symmetric with respect to the axis of symmetry X, or diaphyseal axis. The connection unit 23 can be inserted into the support 12a, advantageously releasably, and coupled with the distal joint element 13, 113 subsequently to the positioning of the support 12a in the humeral seating 51.

In some forms of embodiment, the adapter body 12 can also comprise coupling means to associate the articulation component to the support 12a, that is, to stably connect it for the purposes of articulation. In possible implementations, the coupling means of the adapter body 12 can comprise a concave shaped coupling seating 19, provided in the support 12a, to which the articulation component is coupled, whether it is the humeral head 11 or the concave articular insert 111.

Moreover, the support 12a of the adapter body 12 can comprise a through coupling seating 32 for the connection of the connection unit 23, opposite to the coupling means, to constrain the articulation component. In possible implementations, the through coupling seating 32 can be shaped, for example, for the insertion and the geometric coupling of the connection unit 23.

In possible implementations, the through coupling seating 32 can be internally shaped as a truncated cone, typically with a section that reduces toward the inside of the humeral seating 51.

In some forms of embodiment, the through coupling seating 32 can be configured to allow the insertion and extraction of the distal joint element 13, 113 through the support 12a, without removing the support 12a itself from the humeral seating 51.

Typically, moreover, the through coupling seating 32 can be provided with a diameter greater than the maximum diameter, or maximum equivalent diameter, of the cross section of the distal joint element 13, 113. In this way, the distal joint element 13, 113 can be inserted and can pass completely through the through coupling seating 32.

In possible forms of embodiment, the adapter body 12 can be made completely of metal material, such as alloys of titanium or cobalt.

In other forms of embodiment, the components of the adapter body 12 can be made of different materials, preferably biocompatible with mechanical and chemical properties suitable for the functions provided. Some examples of such materials are, apart from metal materials such as alloys of titanium or cobalt, ceramic materials for medical use or plastic polymer materials, such as polyethylene with high or very high reticulation, or PEEK, possibly loaded with carbon.

According to some forms of embodiment of the present invention, the distal joint element 13, 113 can comprise an insertion portion 14, 114, typically inserted in the humerus 50, and a connection portion 15, for connection to the connection unit 23 of the adapter body 12.

According to some forms of embodiment of the present invention, as described by way of example using FIGS. 1 and 2, the insertion portion 14, 114 and the connection portion 15 can be made as a single body. Typically the distal joint element 13, 113 can be made entirely of metal material suitable for biomedical use, such as for example alloys of titanium or alloys with a cobalt base.

According to other forms of embodiment, the connection portion 15 can be made as a distinct element from the insertion portion 14, 114 and can for example be made with other materials than the insertion portion 14, 114.

According to some forms of embodiment described here, the connection unit 23 can be the modular type, or formed by components, including for example those indicated hereafter by the reference numbers 24, 25, 26, selectively associable with respect to each other.

For example, the connection unit 23 can comprise a clamping element 26, such as for example a bushing, associated, typically in a selectively releasable manner, to the distal joint element 13, 113. In particular, the clamping element 26, can be coupled externally to the distal joint element 13, 113 to clamp a movement of axial extraction thereof toward the outside of the humeral seating 51 with respect to the support 12a. The support 12a in its turn has the through coupling seating 32 configured to clamp an axial movement of the clamping element 26 toward the inside of the humeral seating 51. In particular, the through coupling seating 32 is configured to receive and position the clamping element 26 inside it. For example, the through coupling seating 32 can be mating with the clamping element 26, which therefore can be stably inserted inside it. Moreover, as said above, the through coupling seating 32 is configured to allow the complete passage, for example during the steps of insertion or extraction of the distal joint element 13, 113 into/from the humeral seating 51, advantageously without removing or extracting the support 12a from the humeral seating 51.

According to some forms of embodiment described here, the connection unit 23 can also comprise an anchoring element 24, which can be configured to clamp a movement of axial extraction of the clamping element 26 toward the outside of the humeral seating 51. The anchoring element 24 is for example configured to be constrained, advantageously in a releasable manner, to the support 12a bi-directionally along the axis X. For example, the anchoring element 24 can be provided above the clamping element 26.

In possible implementations (see FIG. 3 for example), the anchoring element 24 can be an externally threaded annular body, which in particular has an external threaded anchoring surface 33 and a shaped central aperture 24a, delimited by an internal drive surface 34, for example polygonal, typically hexagonal, to be driven by a mating key or similar polygonal tool. An advantage of the solution in which the anchoring element 24 is threaded can be that, by means of screwing, it is possible to take the connection unit 23 completely in abutment, that is, packed, preventing unwanted movements of its components, even minimal, which could cause wear.

In other possible implementations, the anchoring element 24 can be an elastically deformable ring, such as an interrupted ring, for example a Seeger ring. For example, in this case the deformable ring can be selectively inserted in a suitable recess made in the through coupling seating 32, such as for example one or more hollows, or an annular groove, typically made above the clamping element 26.

In other possible implementations, the anchoring element 24 can be a deformable portion of the clamping element 26 itself. For example, the clamping element 26 can be suitably coupled to the through coupling seating 32 and in so doing a deformation of the material can be achieved, such as a protruding lip or fin, of the clamping element 26, for example an upper portion thereof, which is selectively constrained in a suitable recess made in the through coupling seating 32 as described above for example.

According to some forms of embodiment described here, the connection unit 23 can also comprise an attachment element 25 associated to the clamping element 26, assembled on the latter for example and which can be attached for example, advantageously in a releasable manner to the distal joint element 13, 113, in particular to the connection portion 15, in order to clamp the axial movement thereof toward the inside of the humeral seating 51 with respect to the clamping element 26. For its connection to the attachment element 25, the connection portion 15 can have an attachment cavity 20.

For example, in possible implementations, the attachment element 25 can be a screw, typically provided with a shaped head 35, circular or polygonal for example. The shaped head 35 can be provided with a blind coupling seating 38, drivable for example by means of a key, typically with a hexagonal head. A threaded rod 36 extends from the shaped head 35, destined to be screwed to the connection portion 15. The attachment cavity 20 of the latter, for example, can be a coordinated threaded seating, to receive the threaded rod 36 of the attachment element 25. In this way, the attachment element 25 can define overall a one-directional constraint of the distal joint element 13, 113 toward the inside of the humeral seating 51.

For example, the attachment element 25 can be inserted through the anchoring element 24, in particular having the shaped head 35 for example housed in the central shaped aperture 24a and the threaded rod 36 protruding from the latter toward the distal joint element 13, 113.

According to other forms of embodiment, the attachment element 25 can provide different configurations, for example with a fixed-joint mechanism. In other possible implementations, the attachment element 25 can be an internally threaded surface of the clamping element 26 configured to cooperate screwing with a mating external threaded surface present on the distal joint element 13, 113, in particular on the connection portion 15.

In possible forms of embodiment, the clamping element 26 can be configured to define an axial stopping abutment for the attachment element 25, in practice preventing movements thereof toward the inside of the humeral seating 51.

In possible forms of embodiment, the clamping element 26 can be inserted between the distal joint element 13, 113 and the anchoring element 24. In particular, the clamping element 26 can be configured to receive the distal joint element 13, 113 inside it through coupling, in particular the connection portion 15 and also part of the attachment element 25 attached to the distal joint element 13, 113, the threaded rod 36 for example.

As we said, the clamping element 26 can also be configured to achieve a same-shape coupling with one-directional constraint toward the inside of the humeral seating 51 with the through coupling seating 32 of the support 12a.

Moreover, the clamping element 26 can be configured to achieve a same-shape coupling with one-directional constraint toward the inside of the humeral seating 51 with the distal joint element 13, 113.

In possible implementations, the clamping element 26 can comprise an internally hollow body to receive the distal joint element 13, 113, in particular the connection portion 15. For example, the clamping element 26 can be shaped as a truncated cone both externally and internally.

For example, the clamping element 26 can comprise a hollow truncated cone element, which has an external clamping surface 41 shaped like a truncated cone with a section that reduces toward the inside of the humeral seating 51. The external clamping surface 41 can define the same-shape coupling with the through coupling seating 32. Moreover, the clamping element 26 shaped like a hollow truncated cone can provide an internal clamping cavity 40, delimited for example by internal lateral walls 43 shaped like a truncated cone inverse with respect to the external clamping surface 41, that is, with a section that widens toward the inside of the humeral seating 51. The internal clamping cavity 40 can define the same-shape coupling with the connection portion 15 of the distal joint element 13, 113. The internal clamping cavity 40 can be sized so that the connection portion 15 does not protrude toward the outside from the clamping element 26. The clamping element 26 can also have an upper clamping surface 42, to define the stopping abutment for the attachment element 25.

In other variants, the clamping element 26 can be shaped externally like a cylinder and internally like a truncated cone, or vice versa. Or again, the clamping element 26 can be shaped like a cylinder both externally and internally. In the case where the clamping element 26 is configured at least internally like a cylinder, a coupling by screwing with the distal joint element 13, 113 can be provided, in particular the connection portion 15, shaped like a cylinder in a coordinated manner, providing one or more suitable threaded surfaces inside the clamping element 26 and outside the distal joint element 13, 113. Moreover, in possible variant forms of embodiment, the clamping element 26 can also have one or more threaded surfaces outside, for coupling with the through coupling seating 32 by screwing.

Therefore, in some forms of embodiment, the clamping element 26 can be coupled to the distal joint element 13, 113 and also the clamping element 26 itself can be coupled to the through coupling seating 32 of the adapter body 12 and can axially clamp the attachment element 25. Furthermore, the clamping element 25 is stably positioned thanks to the attachment element 25 which, being attached to the distal joint element 13, 113, also clamps the clamping element 26 in an intermediate position. Finally, the clamping element 26 is also constrained in its axial movement toward the outside by the anchoring element 24.

Consequently, with the present invention it is possible to position and extract the connection unit 23 and the distal joint element 13, 113 in/from the humeral seating 51, without extracting and removing the support 12a of the adapter body 12.

Indeed, to position the modular humeral prosthesis 10, typically the support 12a of the adapter body 12 can be inserted in the humeral seating 51 suitably prepared.

Moreover, it is possible for example to insert the distal joint element 13, 113 in the clamping element 26 and attach the distal joint element 13, 113 to the attachment element 25, thus obtaining a single insertion body 44. In this condition, the attachment element 25 abuts against the clamping element 26 at the upper part, typically against the upper clamping surface 42.

The single insertion body 44 can be inserted from above into the humeral seating 51, passing through the through coupling seating 32. In this way, the clamping element 26 geometrically couples with the through coupling seating 32 as well.

Then, the anchoring element 24 is positioned from above, which anchors inside the adapter body 12, thus clamping possible movements of the single insertion body 44 toward the outside of the humeral seating 51.

Possible movements of the distal joint element 13, 113 toward the inside of the humeral seating 51 are instead prevented by the upper abutment of the attachment element 25 against the clamping element 26 inserted on the connection portion 15 and interposed between insertion portion 14, 114 and anchoring element 24.

In this way, since the connection unit 23 and the distal joint element 13, 113 can be installed with positioning in sequence from above, that is in antegrade fashion, with the support 12a already positioned in the humeral seating 51, it is also possible to extract, in inverse order, the connection unit 23 and the distal joint element 13, 113, always keeping the support 12a in position.

Similarly, the present invention easily allows operations to remove and/or replace the distal joint element 13, 113 without needing to remove the support 12a disposed in the humeral seating 51, advantageously operating in antegrade fashion. Indeed, it is sufficient to remove the components of the connection unit 23 in sequence, for example first the anchoring element 24 and then the single insertion body 44, formed by the attachment element 25, the clamping element 26 and the distal joint element 13, 113, which is removed through the through coupling seating 32.

Figure 3:
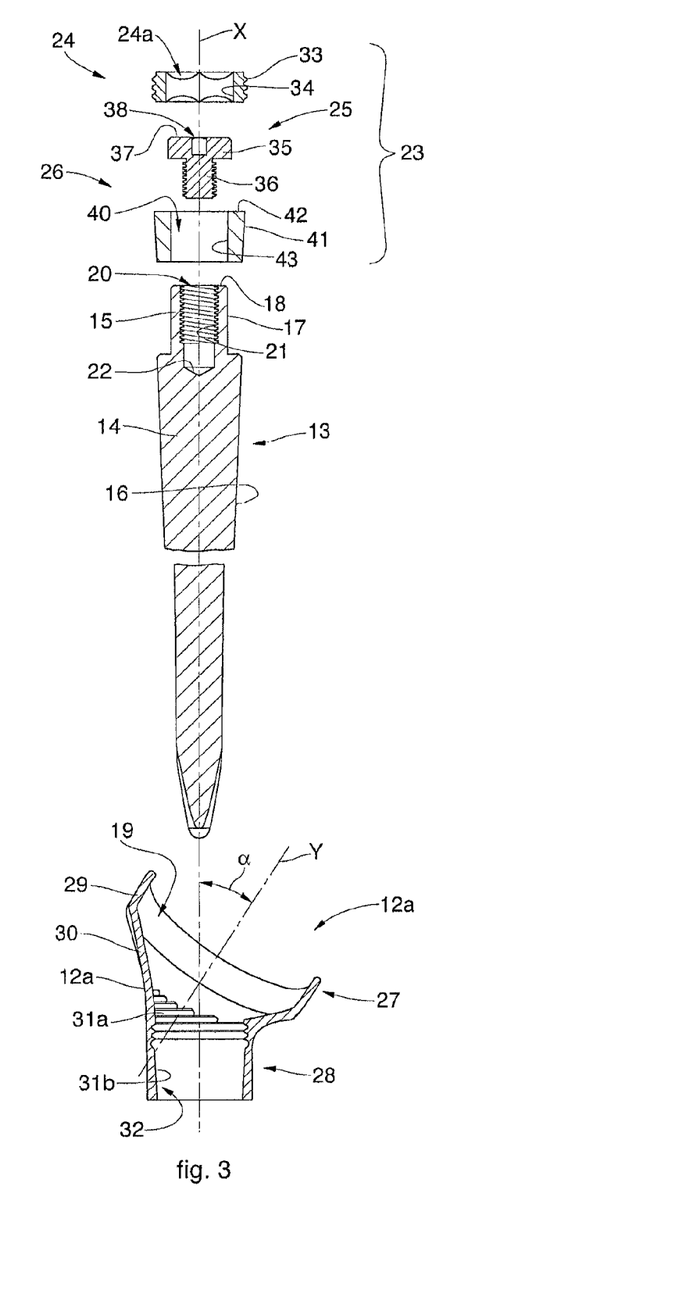
FIG. 3 is a section in separate parts of a modular humeral prosthesis according to forms of embodiment of the present invention.

With reference for example to forms of embodiment described using FIG. 1, 2 or 3, the distal joint element 13, 113 can be an oblong shape and the insertion portion 14 of the distal joint element 13 can therefore be an elongated rod. The insertion portion 14 can be provided with an external insertion surface 16 suitable to be coupled to the internal surface 54 of the humeral seating 51 of the humerus 50.

The coupling of the external insertion surface 16 and the internal surface 54 can generally occur by percussion or by screwing, so as to allow the distal joint element 13 to remain attached to the humerus 50.

According to some variant forms of embodiment, the external insertion surface 16 can comprise a plurality of longitudinal fins, possibly present in only one of its portions, which can allow to increase the interference and the gripping capacity of the contact surfaces. According to another variant the fins are integrated with, or replaced by screw threads.

In the case where the insertion portion 14 has an elongated rod, in a variant solution provided for example to increase the stability and longevity of the graft, the external insertion surface 16 can have a triple or double conical development. According to other solutions, the conicity can be single or with a different multiple value, quadruple for example. The sequence of the conicity is such as to shape the insertion portion 14 overall as a tapered body along the axis X in the insertion direction.

Figure 4:
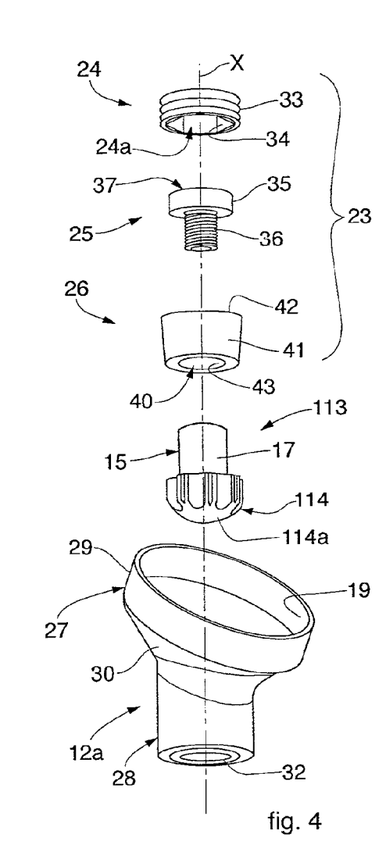
FIG. 4 is a perspective view in separate parts of a modular humeral prosthesis according to other forms of embodiment of the present invention.

With reference for example to forms of embodiment described using FIG. 4, the insertion portion 114 of the distal joint element 113 can be a simple protuberance or reduced protrusion, that is, it can have a reduced size, in particular in length, and for example be suitable for use in mini-invasive humeral prostheses. In particular, in possible implementations, described for example with reference to FIG. 4, the insertion portion 114 can have a front surface shaped like a spherical cap 114a. In other forms of embodiment a different shape of the front end of the insertion portion 114 can be provided, for example conical, truncated cone or cylindrical.

In other possible implementations, the distal joint element 113 can be an antegrade nail which has the insertion portion elongated, insertable in a suitable channel in the humerus 50 for the function of osteosynthesis, and the connection portion 15, for connection to the adapter body 12.

With reference for example to FIG. 3, the connection portion 15 of the distal joint element 13, 113 can comprise an external connection surface 17.

The external connection surface 17 of the connection portion 15 can have a shape complementary to that of the internal clamping cavity 40 of the clamping element 26. For example, the external connection surface 17 can be provided with a truncated cone shape tapered along the axis of symmetry X, toward the outside of the humeral seating 51, as for example described using FIG. 3. In other forms of embodiment, the external connection surface 17 can be shaped as an only partly truncated cone.

The internal clamping cavity 40 of the clamping element 26 can therefore have a truncated cone shape complementary to that of the external connection surface 17 defining a conical coupling.

This conical coupling prevents the clamping element 26 from sliding along the distal joint element 13 toward the insertion portion 14, once they have reached their final positioning shown more clearly in FIG. 1.

With reference for example to FIG. 3, the connection portion 15 can also comprise an upper surface 18 with an annular shape that develops around the attachment cavity 20 inside the distal joint element 13. The attachment cavity 20 is delimited by an internal attachment surface 21 and, for example, by a bottom 22. The internal attachment surface 21 can be cylindrical in shape and have an inner threading.

According to possible forms of embodiment, the support 12a of the adapter body 12 can comprise a proximal portion 27 and a distal portion 28. According to possible forms of embodiment, the proximal portion 27 can be shaped, for example concave, in order to accommodate the humeral head 11 in an anatomical configuration, or a concave articular insert 111 in an inverse configuration. In particular, the proximal portion 27 can have the coupling seating 19. Typically, during normal use the proximal portion 27 can be protruding, that is, on the outside with respect to the humeral seating 51. On the contrary, the distal portion 28 can have the through coupling seating 32. During normal use, the distal portion 28 can be inserted inside the humeral seating 51.

The proximal portion 27 can comprise in its turn an upper portion 29 and a lower portion 30, which can define the coupling seating 19.

The upper portion 29 can be, for example, a seating with a cylindrical shape. The upper portion 29 can have an axial symmetry along an axis Y inclined by an angle α with respect to the axis X, or diaphyseal axis, of the distal joint element 13, 113, to which the adapter body 12 will be connected.

According to some forms of embodiment, moreover, the lower portion 30 can be for example a truncated cone shaped seating.

In possible implementations, the lower portion 30 can provide a hollow truncated cone shape obtained by a cone having the axis Y for its axis of symmetry. Moreover the lower portion 30 can taper starting from the section of the upper portion 29 until it joins the distal portion 28. This form of embodiment, in particular, can define a truncated cone lower portion 30 obtained by sectioning a cone in two planes which are not parallel to each other.

In variant forms of embodiment, the proximal portion 27 of the support 12a is solid (see for example FIG. 3). According to variant forms of embodiment, the proximal portion 27 of the support 12a, in particular the lower portion 30 for example, can provide a configuration such as to allow bone integration, for example with bone fragments of the humerus 50 in the case of reconstruction of a fracture. In possible implementations, described for example with reference to FIG. 5, the proximal portion 27, for example the corresponding lower portion 30, can have through apertures or windows 31 for this purpose, for example defined by lateral support elements 30a which join the upper portion 29 with the distal portion 28. The through apertures or windows 31 can allow to position the bone fragments. In this way, the proximal portion 27 can have a cage configuration for example.

Figure 5:
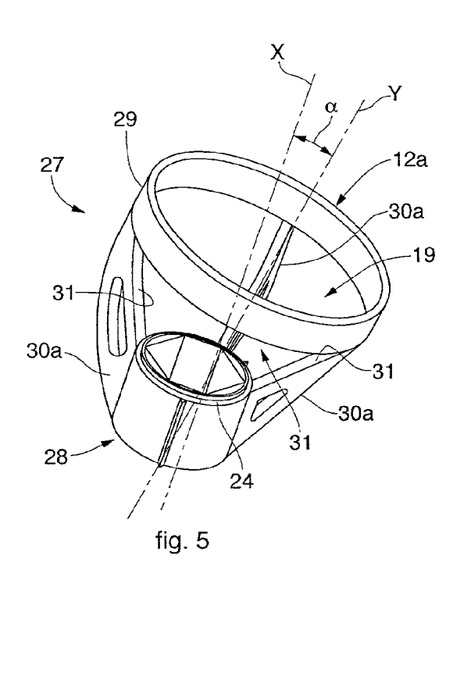
FIG. 5 is a perspective view of a part of a modular humeral prosthesis according to forms of embodiment of the present invention.
Figure 6:
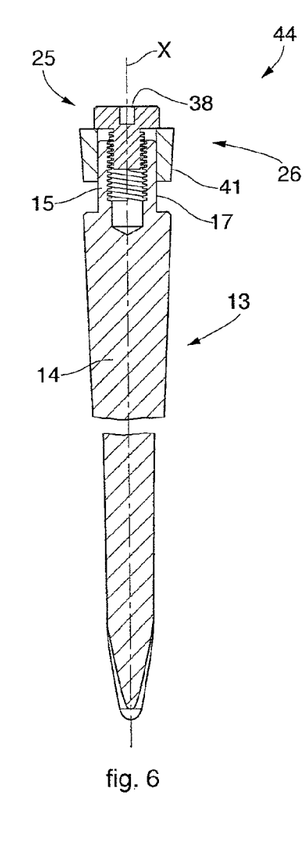
FIG. 6 is a section of a part of a modular humeral prosthesis according to forms of embodiment of the present invention.

With reference to FIG. 5, the upper portion 29 can have a hollow cylindrical shape and the support elements 30a can be a different length and shape from each other.

The support elements 30a can be configured to obtain a desired inclination of the upper portion 29.

For example, providing that the upper portion 29 has a symmetry along an axis Y different to the axis X of symmetry of the distal joint element, an angle α is thus defined between the two axes.

For example, the distal portion 28 of the support 12a, able to connect the connection unit 23 to the support 12a, can be connected to the lower portion 30.

Typically the distal portion 28 can have an axial symmetry along the axis X of symmetry, or diaphyseal axis, of the distal joint element 13, 113. The distal portion 28, in this embodiment, also has an external shape of the cylindrical type, and hollow inside.

According to other forms of embodiment, the distal portion 28 can have other external shapes, keeping the inside hollow, for example parallelepiped or cubic.

In some forms of embodiment, the distal portion 28 can connect to the lower portion 30 of the proximal portion 27, defining a cylinder sectioned in two planes which are not parallel with each other.

The distal portion 28 can provide the through coupling seating 32, able to cooperate with the connection unit 23. According to some forms of embodiment, the through coupling seating 32 can be delimited internally by an upper surface 31a configured to cooperate with the anchoring element 24 and by a lower surface 31b to cooperate with the clamping element 26, in sequence one after the other along the axis X. The upper surface 31a can provide a cylindrical shape for example and have a threading for screwing to the threaded external anchoring surface 33 of the anchoring element 24. The lower distal surface 31b on the contrary can have a truncated cone shape, tapered at the lower part. For example, the external clamping surface 41 of the clamping element 26 can be configured to be coupled with the lower surface 31b, and these surfaces can have complementary shapes. As described for example with reference to FIG. 3, the upper surface 31a and the external clamping surface 41 can both be truncated cone shaped and have the same size, to achieve a conical coupling which prevents the movement of the clamping element 26 along the axis X, in the direction of insertion of the distal body 13, 113 into the adapter body 12, once the clamping element 26 has been inserted in the distal portion 28.

As discussed above, the connection unit 23 of the adapter body 12 is configured to allow the insertion of the distal joint element 13, 113 from the upper part of the adapter body 12, that is, on the side where the humeral head 11 or the concave articular insert 111 are inserted. The distal joint element 13, 113 can therefore be inserted passing first through the proximal portion 27 and then through the proximal portion 28 of the adapter body 12 to then be constrained to the adapter body 12 itself. In possible implementations, the connection unit 23 is provided in the distal portion 28 of the support 12a when the distal joint element 13, 113 is inserted in the adapter body 12.

FIG. 1 is used to describe possible implementations of the modular humeral prosthesis 10 in making an anatomical prosthesis, while FIG. 2 is used to describe possible implementations of the modular humeral prosthesis 10 in making an inverse prosthesis.

With reference for example to FIG. 1, the modular humeral prosthesis 10 can be configured as an anatomical prosthesis to allow the articulation of the humerus 50 in a corresponding glenoid cavity 52, only partly shown, of a shoulder or possibly in a mating artificial seating attached to the glenoid cavity 52.

In the forms of embodiment described by way of example in FIG. 1, the modular humeral prosthesis 10 is shown in an anatomical configuration and comprises a humeral head 11, a distal joint element 13 and an adapter body 12, provided with a connection unit 23, suitable to constrain the humeral head 11 to the distal joint element 13, and with a coupling seating 19.

With reference to forms of embodiment described using FIG. 1 for example, a humeral head 11 which can be associated to the modular prosthesis 10 can be formed by a single body and have a convex articulation surface 11a configured to articulate in the glenoid cavity 52 and a coupling surface 11b to the adapter body 12.

Figure 7:
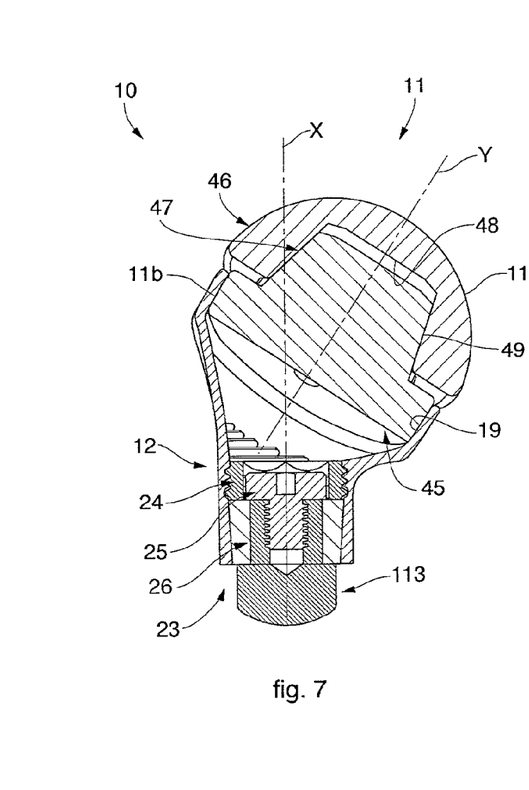
FIG. 7 is a section of a modular humeral prosthesis according to a form of embodiment of the present invention.
Figure 8:
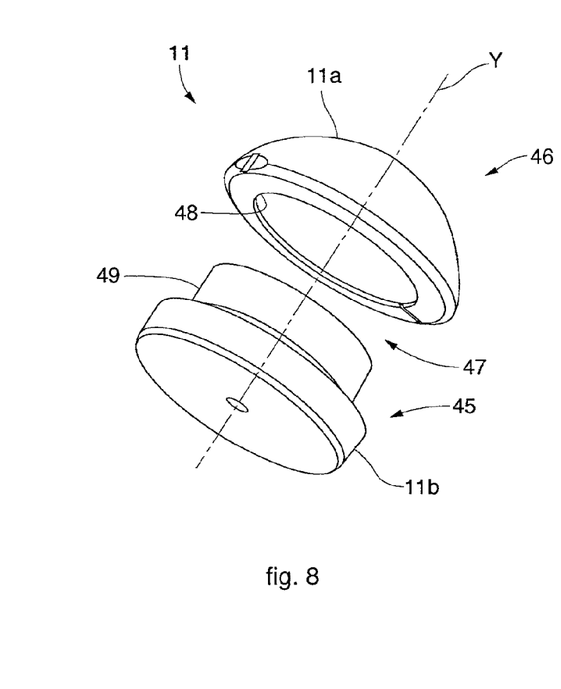
FIG. 8 is a perspective view in separate parts of a part of FIG. 7.

With reference to forms of embodiment described using for example FIGS. 7 and 8, the humeral head 11 can be the modular type, formed by a connection element 45 and by a convex articulation element 46, which can be connected to each other by coupling means 47.

The connection element 45 can have the coupling surface 11b and is inserted for example in the upper portion 29 to support the convex articulation element 46, which, on the contrary, is the part nearest the glenoid cavity 52, and has the convex articulation surface 11a.

The coupling means 47 can comprise a coupling cavity 48, made in the convex articulation element 46, and a coupling pin 49 provided protruding from the connection element 45. For example, the coupling cavity 48 and the coupling pin 49 are configured to achieve a conical coupling.

Instead, with reference to FIG. 2 for example, the modular humeral prosthesis 10 can be configured as an inverse prosthesis to allow the articulation of the humerus 50 with respect to an artificial convex portion, semi-spherical for example, also called glenosphere, positioned in the glenoid.

In the forms of embodiment described by way of example in FIG. 2, a concave articular insert 111 is provided, able to be used in a modular humeral prosthesis 10 in an inverse configuration, constrained to the adapter body 12, as an alternative to the humeral head 11 in FIGS. 1, 7 and 8.

With reference to forms of embodiment described using FIG. 2 for example, the concave articular insert 111 associable to the modular humeral prosthesis 10, in the inverse configuration, can have a concave articulation surface 111a, for example to allow the articulation of a glenosphere attached to the glenoid cavity 52, and a support surface 111b to be inserted and attached in the adapter body 12.

It is clear that modifications and/or additions of parts may be made to the modular humeral prosthesis 10 as described heretofore, without departing from the field and scope of the present invention.

It is also clear that, although the present invention has been described with reference to some specific examples, a person of skill in the art shall certainly be able to achieve many other equivalent forms of humeral prosthesis, having the characteristics as set forth in the claims and hence all coming within the field of protection defined thereby.

The invention claimed is:

1. Modular humeral prosthesis suitable for implant in a humeral seating of a humerus, comprising an articulation component, a distal joint element able to be inserted into said humeral seating along an insertion axis, and an adapter body provided with a support positionable in the humeral seating and that has a coupling seating to connect said articulation component and provided with a connection unit inserted into said connect said distal joint element to said adapter body in a releasable manner, wherein said connection unit comprises:

a clamping element associated in a selectively releasable manner to the distal joint element, an anchoring element configured to clamp the clamping element against axial extraction movement in an axial direction toward the outside of the humeral seating, an attachment element associated with the clamping element and the distal joint element to clamp the distal joint element in an axial direction toward the inside of the humeral seating, wherein said support has a through coupling seating configured to receive and position said clamping element inside it, and also configured to allow the insertion and extraction of said distal joint element through said support without removing said support from the humeral seating; and wherein the clamping element has a truncated cone configuration, both internally and externally.

2. Humeral prosthesis as in claim 1, wherein the clamping element is configured to prevent axial extraction movement of the distal joint element toward the outside of the humeral seating.

3. Humeral prosthesis as in claim 1, wherein the clamping element cooperates with the through coupling seating to achieve a same-shape coupling defined at least in part by an inclined truncated cone, the clamping element and the through coupling seating further cooperating to prevent axial movement of the through coupling seating in a direction toward the outside of the humeral seating.

4. Humeral prosthesis as in claim 1, wherein the clamping element is configured to achieve a same-shape coupling with the distal joint element to clamp the distal joint element in the axial direction.

5. Humeral prosthesis as in claim 1, wherein the clamping element is coupled externally to the distal joint element.

6. Humeral prosthesis as in claim 1, wherein the clamping element comprises a hollow truncated cone element that has an external clamping surface shaped like a truncated cone with a section that reduces toward the inside of the humeral seating, an internal clamping cavity delimited by internal lateral walls shaped like a truncated cone inverse with respect to the external clamping surface, to receive a mating connection portion of the distal joint element.

7. Humeral prosthesis as in claim 1, wherein the clamping element is inserted between the distal joint element and the anchoring element.

8. Humeral prosthesis as in claim 1, wherein the attachment element is mounted on the clamping element and is attached to the distal joint element.

9. Humeral prosthesis as in claim 1, wherein the attachment element comprises a screw, provided with a shaped head, configured to abut against the clamping element, from which a threaded rod extends, configured to be inserted into the clamping element and able to be screwed into an attachment cavity of the distal joint element to clamp the distal joint element in the axial direction.

10. Humeral prosthesis as in claim 1, wherein the clamping element is configured to define an axial stopping abutment for the attachment element.

11. Modular humeral prosthesis suitable for implant in a humeral seating of a humerus, comprising an articulation component, a distal joint element able to be inserted into said humeral seating along an insertion axis, and an adapter body provided with a support positionable in the humeral seating and that has a coupling seating to connect said articulation component and provided with a connection unit inserted into said support to connect said distal joint element to said adapter body in a releasable manner, wherein said connection unit comprises:
　a clamping element associated in a selectively releasable manner to the distal joint element,
　an anchoring element configured to clamp the clamping element against axial extraction movement in an axial direction toward the outside of the humeral seating,
　an attachment element associated with the clamping element and the distal joint element to clamp the distal joint element in an axial direction toward the inside of the humeral seating,
　wherein said support has a through coupling seating configured to receive and position said clamping element inside it, and also configured to allow the insertion and extraction of said distal joint element through said support without removing said support from the humeral seating; and
　wherein internally the clamping element has a cylindrical configuration and externally a truncated cone configuration.

12. Humeral prosthesis as in claim 11, wherein at least internally the clamping element has threaded connection means to cooperate with the distal joint element.

13. Modular humeral prosthesis suitable for implant in a humeral seating of a humerus, comprising an articulation component, a distal joint element able to be inserted into said humeral seating along an insertion axis, and an adapter body provided with a support positionable in the humeral seating and that has a coupling seating to connect said articulation component and provided with a connection unit inserted into said support to connect said distal joint element to said adapter body in a releasable manner, wherein said connection unit comprises:
　a clamping element associated in a selectively releasable manner to the distal joint element,
　an anchoring element configured to clamp the clamping element against axial extraction movement in an axial direction toward the outside of the humeral seating,
　an attachment element associated with the clamping element and the distal joint element to clamp the distal joint element in an axial direction toward the inside of the humeral seating,
　wherein said support has a through coupling seating configured to receive and position said clamping element inside it, and also configured to allow the insertion and extraction of said distal joint element through said support without removing said support from the humeral seating; and
　wherein the clamping element has a cylindrical configuration both internally and externally.

14. Modular humeral prosthesis suitable for implant in a humeral seating of a humerus, comprising an articulation component, a distal joint element able to be inserted into said humeral seating along an insertion axis, and an adapter body provided with a support positionable in the humeral seating and that has a coupling seating to connect said articulation component and provided with a connection unit inserted into said support to connect said distal joint element to said adapter body in a releasable manner, wherein said connection unit comprises:
　a clamping element associated in a selectively releasable manner to the distal joint element,
　an anchoring element configured to clamp the clamping element against axial extraction movement in an axial direction toward the outside of the humeral seating,
　an attachment element associated with the clamping element and the distal joint element to clamp the distal joint element in an axial direction toward the inside of the humeral seating,
　wherein said support has a through coupling seating configured to receive and position said clamping element inside it, and also configured to allow the insertion and extraction of said distal joint element through said support without removing said support from the humeral seating; and
　wherein the clamping element has a truncated cone configuration, both internally and externally; and
　wherein the anchoring element comprises an externally threaded annular body that has a threaded external anchoring surface and a shaped central aperture.

15. Modular humeral prosthesis suitable for implant in a humeral seating of a humerus, comprising an articulation component, a distal joint element able to be inserted into said humeral seating along an insertion axis, and an adapter body provided with a support positionable in the humeral seating and that has a coupling seating to connect said articulation component and provided with a connection unit inserted into said support to connect said distal joint element to said adapter body in a releasable manner, wherein said connection unit comprises:
　a clamping element associated in a selectively releasable manner to the distal joint element, an anchoring element configured to clamp the clamping element against axial extraction movement in an axial direction toward the outside of the humeral seating, an attachment element associated with the clamping element and the distal joint element to clamp the distal joint element in an axial direction toward the inside of the humeral seating, wherein said support has a through coupling seating configured to receive and position said clamping element inside it, and also configured to allow the insertion and extraction of said distal joint element through said support without removing said support from the humeral seating; and wherein the clamping element has a truncated cone configuration, both internally and externally; and wherein the anchoring element comprises an elastically deformable ring.

16. Humeral prosthesis as in claim 15, wherein the elastically deformable ring comprises a Seeger ring.

* * * * *